United States Patent [19]

Siegel et al.

[11] Patent Number: 4,761,252
[45] Date of Patent: Aug. 2, 1988

[54] PROCESS FOR THE PREPARATION OF VINYLPHOSPHONIC DICHLORIDE

[75] Inventors: Herbert Siegel; Erwin Weiss, both of Hofheim am Taunus; Harald Berger, Kelkheim, all of Fed. Rep. of Germany

[73] Assignee: Hoechst Aktiengesellschaft, Frankfurt am Main, Fed. Rep. of Germany

[21] Appl. No.: 90,229

[22] Filed: Aug. 27, 1987

[30] Foreign Application Priority Data

Aug. 30, 1986 [DE] Fed. Rep. of Germany ....... 3629578

[51] Int. Cl.<sup>4</sup> ............................................... C07F 9/42
[52] U.S. Cl. .......................... 260/543 P; 260/502.4 R
[58] Field of Search ..................................... 260/543 P

[56] References Cited

U.S. PATENT DOCUMENTS 4,548,762 10/1985 Kleiner ............................ 260/543 P

FOREIGN PATENT DOCUMENTS 695500 10/1964 Canada ............................ 260/543 P
698910 12/1964 Canada ............................ 260/543 P
2175904 12/1986 United Kingdom ............ 260/543 P Primary Examiner—Paul J. Killos

[57] ABSTRACT

The invention relates to a process for the preparation of vinylphosphonic dichloride, in which a 2-chloroethanephosphonate of the formula

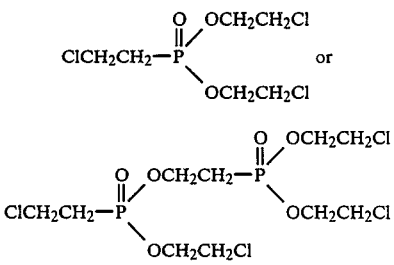

or a mixture of the two esters, is reacted with thionyl chloride at a temperature of 60° to 160° C. in the presence of a catalyst which contains tertiary phosphines, quaternary ammonium or phosphonium salts or alkali metal or alkaline-earth metal halides.

During this reaction, any thionyl chloride which may be present is removed by distillation subsequent to this reaction, the mixture remaining is heated to 140° to 200° C., and the vinylphosphonic dichloride produced during this is removed by distillation.

7 Claims, No Drawings

PROCESS FOR THE PREPARATION OF VINYLPHOSPHONIC DICHLORIDE

DESCRIPTION

The invention relates to a process for the preparation of vinylphosphonic dichloride. Through hydrolysis of this, vinylphosphonic acid is obtained, which is an important intermediate in the preparation of flameproofing agents and an important monomer in the preparation of homo- or copolymers. Such polymers are important in paints, plastics, corrosion inhibitors and coating agents.

German Offenlegungsschrift No. 1,568,945 discloses that vinylphosphonic dichloride can be prepared from 2-chloroethanephosphonic dichloride through elimination of HCl in the presence of triphenyl phosphine. Furthermore, U.S. Pat. No. 4,213,922 discloses that 2-chloroethanephosphone dichloride can be prepared from bis-chloroethyl 2-chloroethanephosphate

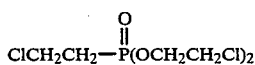

with the aid of thionyl chloride; in this reaction, tertiary amines, N,N-disubstituted formamides or N,N-disubstituted phosphoric triamides are employed as catalysts. German Offenlegungsschrift No. 2,132,962 discloses the same reaction using phosgene in place of thionyl chloride: tertiary phosphines and quaternary ammonium or phosphonium salts, inter alia, are employed as catalysts.

However, the preparation of vinylphosphonic dichloride from bis-chloroethyl 2-chloroethanephosphonate is not described in any of the literature citations mentioned. Surprisingly, it has been found that this preparation succeeds without isolation of the 2-chloroethanephosphonic dichloride produced as an intermediate and without addition of basic auxiliaries for elimination of HCl with the aid of thionyl chloride in the presence of tertiary phosphines, quaternary ammonium or phosphonium salts or alkali metal or alkaline-earth metal halides.

The invention accordingly relates to a process for the preparation of vinylphosphonic dichloride, wherein a 2-chloroethanephosphonate of the formula

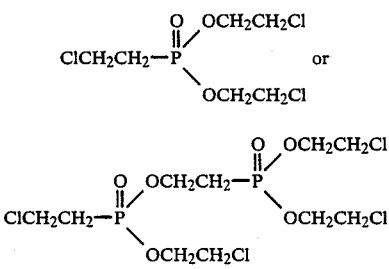

or a mixture of the two esters, is reacted with thionyl chloride at a temperature of 60° to 160° C. in the presence of a catalyst which contains at least one of the following substances:

(a) tertiary phosphines of the general formula

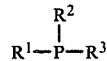

in which the radicals $R_1$, $R_2$ and $R_3$ may be identical or different and denote straight-chain or branched $C_1$–$C_{10}$-alkyl, optionally substituted by $C_1$–$C_4$-alkoxy, $C_1$–$C_4$-alkylthio or $C_1$–$C_4$-dialkylamino radicals, or denote phenyl, optionally substituted by halogen, $C_1$–$C_4$-alkyl or $C_1$–$C_4$-alkoxy radicals, (b) quaternary ammonium or phosphonium salts of the general formula

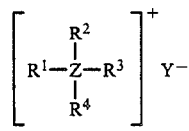

where $Z = N$ or $P$, where $Y^-$ is an anion of a strong acid and in which $R_1$, $R^2$ and $R^3$ have the meaning mentioned in the case of (a) and $R^4$ denotes straight-chain or branched $C_1$–$C_{10}$-alkyl, or benzyl which is substituted by halogen, $C_1$–$C_4$-alkyl or $C_1$–$C_4$-alkoxy radicals, (c) alkali metal or alkaline-earth metal halides, any thionyl chloride which may still be present is removed by distillation subsequent to this reaction, the mixture remaining is heated to 140° to 200° C., and the vinylphosphonic dichloride produced during this is removed by distillation.

$R^1$, $R_2$ and $R^3$ are preferably $C_1$–$C_4$-alkyl radicals (optionally substituted as specified above) or phenyl radicals (optionally substituted as specified above). $R^4$ is preferably a $C_1$–$C_4$-alkyl radical or benzyl which is substituted by halogen, $C_1$–$C_4$-alkyl or $C_1$–$C_4$-alkoxy radicals.

The reaction of the ester or esters with thionyl chloride is carried out at 60°–160° C., preferably 60°–140° C., in particular 80°–130° C.

The thionyl chloride to ester employed molar ratio is 2:1 to 4:1, preferably 2.5:1 to 3.5:1. The amount of catalyst is 0.1 to 10 mole percent, preferably 0.5 to 2 mole percent, relative to the ester employed.

Particularly suitable catalysts are the following tertiary phosphines: triphenyl phosphine, tris(4-fluorophenyl) phosphine, tris(4-tolyl) phosphine, tris(4-methoxyphenyl) phosphine, (N,N-diethyl)aminomethyldiphenyl phosphine, tri-n-butyl phosphine and bis(4-methoxyphenyl)methyl phosphine. Triphenyl phosphine is very particularly suitable.

Suitable anions $Y^-$ of a strong acid in the formula for the quaternary ammonium or phosphonium salts are, for example, $Cl^-$, $Br^-$, $I^-$, $NO_3$, $SO_4$, $HSO_4$ and $PO_4$, i.e. the symbol $Y^-$ shall also represent polyvalent anions.

Amongst the quaternary ammonium and phosphonium salts, those which are used in phase-transfer catalysis, for example tetrabutylammonium bromide, tetrabutylphosphonium bromide, tetrabutylammonium hydrogen sulfate, methyltrioctylammonium chloride, benzyltrimethylammonium bromide and benzyltriethylammonium chloride, are particularly suitable as catalysts. Tetrabutylammonium bromide and tetrabutylphosphonium bromide are very particularly suitable.

Amongst the alkali metal or alkaline-earth metal halides, lithium bromide is particularly suitable as catalyst.

In order to ensure an adequate reaction time for the relatively inert phosphonates, the thionyl chloride is preferably introduced into the initially introduced ester. The thionyl chloride is particularly preferably introduced into the initially introduced ester at the base of the reaction vessel. The dichloroethane eliminated during the reaction, which is removed by distillation at the reaction temperature produced and which, with increasing conversion, carries thionyl chloride out of the reaction vessel, is preferably condensed and recycled. Through the circulation thus caused of the unreacted thionyl chloride, the latter is utilized in an optimum fashion.

The reaction can also be carried out in the presence of an inert solvent. Examples which may be mentioned are: chlorobenzene, dichlorobenzene or hydrocarbons. The reaction is now also preferably carried out at 80° to 130° C.

The end of the reaction is recognized from the evolution of SO₂ and HCl ceasing.

The dichloroethane produced and, if appropriate, the unreacted thionyl chloride are subsequently removed by distillation, the mixture remaining is heated to 140° to 200° C., and the vinylphosphonic dichloride produced during this is removed by distillation.

The following examples are intended to illustrate the invention. Crude bis-2-chloroethyl 2-chloroethanephosphonate, as obtained on Arbusov rearrangement of tris-2-chloroethyl phosphite P(OCH₂CH₂Cl)₃ (German Offenlegungsschrift No. 2,132,962: Houben-Weyl, Volume XII/1 (1963), page 389) by heating to 140° C., was used as starting material. About 55% of the crude ester was bis-2-chloroethyl 2-chloroethanephosphonate

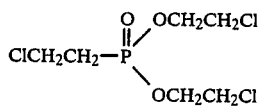

and about 38% was mono-2chloroethyl mono(bis-2-chloroethyl 2-chloroethanephosphonate) 2-chloroethanephosphonate

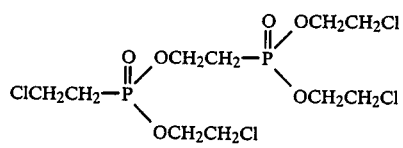

The initial quantities and the yield were related to the pure content of 93%.

EXAMPLE 1

500 g of crude bis-chloroethyl 2-chloroethanephosphonate and 497 g (4.18 mol) of thionyl chloride were heated to 115° C. within 30 minutes in the presence of 5 g of triphenyl phosphine. Dichloroethane and thionyl chloride distilling off were condensed in a receiver and continuously fed back into the reaction mixture for 7 hours via a dip tube at the base of the reaction vessel. The volatile components were subsequently removed by distillation at 125° C., initially at atmospheric pressure and then at 300 mbar. 347.8 g of distillate were obtained, of which 81% were dichloroethane and 19% were unreacted thionyl chloride. For elimination of HCl, the 2-chloroethanephosphonic dichloride remaining was heated at 140° C. and 120 mbar for 5 hours. During this time, 215.2 g (79% of theory) of vinylphosphonic dichloride of boiling point 88°–93° C. distilled over.

EXAMPLE 2

100 g of crude bis-chloroethyl 2-chloroethanephosphonate and 99.4 g (0.835 mol) of thionyl chloride were heated to 125° C. within 30 minutes in the presence of 1.0 g (0.003 mol) of tetrabutylammonium bromide. Dichloroethane and thionyl chloride distilling off were condensed in a receiver and continuously fed back into the reaction mixture for 6 hours via a dip tube at the base of the reaction vessel. The volatile components were subsequently removed by distillation at 128° C., initially at atmospheric pressure and then at 100 mbar. 69.7 g of distillate were obtained, of which 81% were dichloroethane and 19% were unreacted thionyl chloride. For elimination of HCl, the 2-chloroethanephosphonic dichloride remaining was heated to 185° C., 40.8 g (0.28 mol, 76% of theory) of vinylphosphonic dichloride distilling over within one hour at 166°–167° C.

EXAMPLE 3

Analogously to Example 2, 100 g of crude bis-chloroethyl 2-chloroethanephosphonate were reacted with 99.4 g (0.835 mol) of thionyl chloride at 127° C. in the presence of 1.0 g (0.003 mol) of tetrabutylphosphonium bromide. 68.7 g of a preliminary fraction were obtained, of which 86% were dichloroethane and 14% were unreacted thionyl chloride. Heating the crude 2-chloroethanephosphonic dichloride remaining to 185° C. gave, within one hour, 39.0 g (0.27 mol, 73% of theory) of vinylphosphonic dichloride, which distilled over at 166°–167° C.

EXAMPLE 4

Analogously to Example 2, 150 g of crude bis-chloroethyl 2-chloroethanephosphonate were reacted with 149.1 g (1.25 mol) of thionyl chloride at 125° C. in the presence of 2.0 g (0.05 mol) of lithium bromide. 109.8 g of a preliminary fraction were obtained, of which 86% were dichloroethane and 14% were unreacted thionyl chloride. By heating the crude 2-chloroethanephosphonic dichloride remaining to 190° C., 62.1 g (0.43 mol, 77% of theory) of vinylphosphonic dichloride, which distilled over at 165°–167° C., were obtained within 2 hours.

We claim:

1. A process for the preparation of vinylphosphonic dichloride, wherein a 2-chloroethanephosphonate of the formula

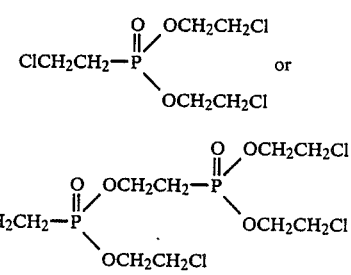

or a mixture of the two esters, is reacted with thionyl chloride at a temperature of 60° to 160° C. in the presence of a catalyst which contains at least one of the following substances:

(a) tertiary phosphines of the general formula $R^1$-$P(R^2)$-$R^3$ in which the radicals $R^1$, $R^2$ and $R^3$ may be identical or different and denote straight-chain or branched $C_1$-$C_{10}$-alkyl, which is unsubstituted or substituted by $C_1$-$C_4$-alkoxy, $C_1$-$C_4$-alkylthio or $C_1$-$C_4$-dialkylamino radicals, or denote phenyl, which is unsubstituted or substituted by halogen, $C_1$-$C_4$-alkyl or $C_1$-$C_4$-alkoxy radicals, (b) quaternary ammonium or phosphonium salts of the general formula

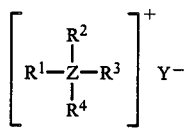

where $Z=N$ or $P$, where $Y^-$ is an anion of a strong acid and in which $R^1$, $R^2$ and $R^3$ have the meaning mentioned in the case of (a) and $R^4$ denotes straight-chain or branched $C_1$-$C_{10}$-alkyl, or benzyl which is substituted by halogen, $C_1$-$C_4$-alkyl or $C_1$-$C_4$-alkoxy radicals, (c) alkali metal or alkaline-earth metal halides, any thionyl chloride which may still be present is removed by distillation subsequent to this reaction, the mixture remaining is heated to 140° to 200° C., and the vinylphosphonic dichloride produced during this is removed by distillation.

2. The process as claimed in claim 1, wherein the reaction of the ester or esters with thionyl chloride is carried out at 60°–140° C.

3. The process as claimed in claim 1, wherein the reaction of the ester or esters with thionyl chloride is carried out at 80°–130° C.

4. The process as claimed in claim 1, wherein the catalyst employed is triphenyl phosphine, tetrabutylammonium bromide, tetrabutylphosphonium bromide or lithium bromide.

5. The process as claimed in claim 1, wherein the dichloroethane eliminated and removed by distillation during the reaction of the ester or esters with thionyl chloride is condensed and recycled.

6. The process as claimed in claim 1, wherein the thionyl chloride is introduced into the initially introduced ester.

7. The process as claimed in claim 1, wherein the thionyl chloride is introduced into the initially introduced ester at the base of the reaction vessel.

* * * * *